(12) United States Patent
He et al.

(10) Patent No.: US 9,446,091 B2
(45) Date of Patent: Sep. 20, 2016

(54) CASPOFUNGIN OR SALTS THEREOF WITH HIGH PURITY, AS WELL AS PREPARATION METHOD AND USE THEREOF

(75) Inventors: Bingming He, Shanghai (CN); Ming Li, Shanghai (CN); Zhijun Tang, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 14/113,296

(22) PCT Filed: Apr. 20, 2012

(86) PCT No.: PCT/CN2012/074420
§ 371 (c)(1),
(2), (4) Date: Jan. 16, 2014

(87) PCT Pub. No.: WO2012/142959
PCT Pub. Date: Oct. 26, 2012

(65) Prior Publication Data
US 2014/0128315 A1    May 8, 2014

(30) Foreign Application Priority Data
Apr. 22, 2011 (CN) .......................... 2011 1 0101870

(51) Int. Cl.
*C07K 7/56* (2006.01)
*A61K 38/12* (2006.01)
*A61K 38/00* (2006.01)
*C07K 7/54* (2006.01)
*A61K 31/19* (2006.01)

(52) U.S. Cl.
CPC .............. *A61K 38/12* (2013.01); *A61K 31/19* (2013.01); *A61K 38/005* (2013.01); *C07K 7/54* (2013.01); *C07K 7/56* (2013.01)

(58) Field of Classification Search
None
See application file for complete search history.

(56) References Cited

U.S. PATENT DOCUMENTS

| | | | |
|---|---|---|---|
| 5,552,521 A | 9/1996 | Belyk et al. | |
| 5,936,062 A | 8/1999 | Leonard et al. | |
| 5,952,300 A * | 9/1999 | Nerurkar et al. | 514/3.3 |
| 2001/0038824 A1* | 11/2001 | Horii et al. | 424/43 |
| 2009/0170753 A1* | 7/2009 | Welz et al. | 514/9 |
| 2010/0168415 A1 | 7/2010 | Lee et al. | |
| 2013/0184433 A1* | 7/2013 | De Pater et al. | 530/321 |

FOREIGN PATENT DOCUMENTS

| | | |
|---|---|---|
| CN | 101305018 | 11/2008 |
| CN | 101516387 | 8/2009 |
| CN | 101648994 | 2/2010 |
| CN | 101792486 | 8/2010 |
| EP | 1785432 | 5/2007 |
| WO | 94/21677 | 9/1994 |
| WO | 96/24613 | 8/1996 |
| WO | 97/47645 | 12/1997 |
| WO | 02/083713 | 10/2002 |
| WO | 2009/151341 | 12/2009 |
| WO | 2009/158034 | 12/2009 |
| WO | 2010/008493 | 1/2010 |
| WO | 2010/064219 | 6/2010 |
| WO | 2010/108637 | 9/2010 |

OTHER PUBLICATIONS

W. R. Leonard et al., "Synthesis of the Antifungal β-1,3-Glucan Synthase Inhibitor Cancidas (Caspofungin Acetate) from Pneumocandin $B_0$" J. Org. Chem. (2007), vol. 72, p. 2335-2343.
International Search Report for International Application No. PCT/CN2012/074420, dated Jul. 5, 2012 (3 pages).
Written Opinion for International Application No. PCT/CN2012/074420, dated Jul. 5, 2012 (5 pages).

* cited by examiner

*Primary Examiner* — Jeffrey E Russel
(74) *Attorney, Agent, or Firm* — Hamre, Schumann, Mueller & Larson, P.C.

(57) ABSTRACT

Disclosed are a high purity of caspofungin or salts thereof, and a preparation method thereof, and use thereof. Disclosed are a caspofungin or salts thereof with low solvent residue and hyposaline, and a preparation process comprising: dissolving a crude product of caspofungin or salts thereof into a system of water and acetic acid, then mixing with a first organic solvent ethyl alcohol, subsequently mixing with a second organic solvent ethyl acetate, then being subject to filtration and drying together with water, to obtain caspofungin or salts thereof with high stability, low solvent residue and hyposaline.

10 Claims, 3 Drawing Sheets

CASPOFUNGIN OR SALTS THEREOF WITH HIGH PURITY, AS WELL AS PREPARATION METHOD AND USE THEREOF

TECHNICAL FIELD

The present invention relates to the field of organic chemistry, particularly to caspofungin or the salts thereof as well as the preparation method thereof.

BACKGROUND

In 1974, it was discovered that echinocandin compounds possess excellent antibacterial activity. Thereafter, many semisynthetic echinocandin compounds have been studied for their pharmacologic activities. In 2001, caspofungin was approved by US FDA, which represents the landmark for the research of antifungal medicaments. Caspofungin, the chemical structure of which is shown by Formula 1, represents a broad-spectrum and low-toxic medicament with unique action site:

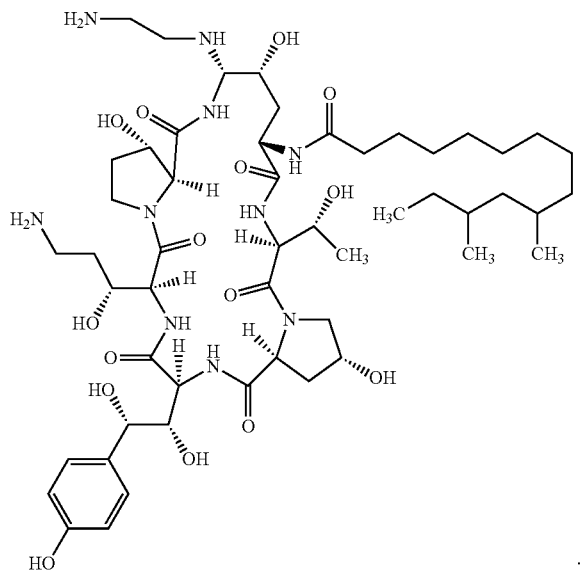

1

Caspofungin analogs and the preparation of Caspofungin have been described in WO94/21677, WO96/24613, U.S. Pat. No. 5,552,521, WO97/47645, U.S. Pat. No. 5,936,062, WO02/083713, J. Org. Chem., 2007, 72, 2335-2343, CN101792486A, CN101648994A, WO2010008493A2, US2010168415A1, EP1785432, WO2010064219A1, WO2009158034A1, WO2009151341A1 and WO2010108637A1. The solvent residue and salt residue in Caspofungin should be strictly limited in the form of injections. However, caspofungin has poor stability, therefore, for preventing caspofungin from degrading, special methods are generally used to remove the residual solvent in it.

Methods for drying caspofungin using humid nitrogen have been reported in J. Org. Chem., 2007, 72, 2335-2343, U.S. Pat. No. 5,552,521, U.S. Pat. No. 5,936,062, WO96/24613 and EP1785432. However, there are some disadvantages for these methods, such as high cost, poor reproducibility, huge waste of nitrogen, and high residue of solvent, which do not comply with the quality requirement of medicaments.

Methods for drying caspofungin by lyophilization have been reported in WO94/21677, WO97/47645, CN101792486A, US2010168415A1, CN101648994A and WO2009158034A1. Amorphous caspofungin is obtained by the methods, and the disadvantages of which are poor stability and high solvent residue. The methods could hardly meet the requirements for industrialization due to the high cost, great energy consumption, low efficiency, and the limited productivity.

Spray drying method has been reported in WO2010008493A2, wherein a solution is sprayed into droplets in hot air flow, thereby evaporating the water or solvent contained in the solution rapidly. However, upon research, the present inventors have found that the resulting product is still amorphous caspofungin with poor stability; and the solvents, such as ethanol and ethyl acetate can not be removed thoroughly; and the solvent residue greatly exceeds the limit. Moreover, the method is unsuitable for industrialization due to the high cost for the necessary equipments, and the limitation of production scale.

The method for drying caspofungin by vacuum drying has been reported in WO2009151341A1. During the early stage of drying, the organic solvent contained in the sample can be readily removed; however, crystal lattice of the sample will gradually close with the reduction of residual solvent, resulting in the solvent retention in the crystal lattice. In the late stage of drying, crystal lattice of the sample will totally close, resulting in the solvent being retained in the crystal lattice permanently and unable to be removed. Additionally, during the procedure of drying, the stability of sample will decrease with the reduction of water content, therefore, the sample will degrade and caspofungin with high purity can not be obtained.

Salting-out crystallization of caspofungin has been reported in WO2010108637A1. The residual solvent is not present in the caspofungin obtained by the method, however, the content of salt in the product will inevitably exceed the limit, and the sample will degrade during the crystallization, therefore, the purity of product will be reduced, and the product can not be used as raw material for market supply or for the preparation of pharmaceutical formulation.

According to ICH (International Conference on Harmonization of Technical Requirements for Registration of Pharmaceuticals for Human Use), the residual solvent in drug is defined as volatile organic compounds produced or used during the production of raw medicine or excipients or the preparation of formulation, which can not be removed thoroughly. In the Guideline, the residual solvent is classified according to the harm extent, under the conditions for ensuring the safety of human, the acceptable amount, i.e., limit, of residual solvent is established, and the toxicologically acceptable level of residual solvent is proposed.

Generally, many solvents, such as tetrahydrofuran, acetonitrile, methanol, ethyl acetate and ethanol, will be used in the current process for producing caspofungin. However, the caspofungin product prepared by the routine methods said above can not comply with the requirements of residual solvent stipulated in ICH (see ICH Q3C).

Therefore, there are defects for each current preparation method for caspofungin, such as high cost for instrument, limited production scale, difficulties in operation and unsuitability for industrialization. The resulting product has poor stability, therefore, it should be stored below −70° C., which will result in difficulties in transportation of product and industrialization, and will restrict the production scale of industrialization. Therefore, it is urgent to develop a preparation method for caspofungin or salts thereof, and said method can efficiently remove the residual solvent in caspofungin, prevent caspofungin from degrading, and is suitable for industrialization, thereby obtaining caspofungin or salts thereof which is stable and with low solvent residue and complies with the medical standards.

SUMMARY OF THE INVENTION

The subject of the present invention is to provide caspofungin or salts thereof with low solvent residue.

Another subject of the present invention is to provide caspofungin or salts thereof with hyposaline.

Another subject of the present invention is to provide a method for producing caspofungin or salts thereof with low solvent residue and hyposaline.

The last subject of the present invention is to provide the use of caspofungin or salts thereof with low solvent residue and hyposaline.

In the first aspect of the present invention, caspofungin of formula 1 or salts thereof with low solvent residue and hyposaline is provided, wherein the weight percentage of tetrahydrofuran, acetonitrile, methanol, ethyl acetate and ethanol is lower than 0.072%, 0.041%, 0.3%, 0.5% and 0.5%, respectively, preferably, lower than 0.05%, 0.02%, 0.15%, 0.25% and 0.25%, more preferably, lower than 0.02%, 0.01%, 0.05%, 0.10% and 0.10%, and, most preferably, the weight percentage of tetrahydrofuran, acetonitrile, methanol, ethyl acetate and ethanol is 0%; the content of other solvents complies with the requirements of residual solvent stipulated in ICH; and the weight percentage of inorganic salts (determined by residue on ignition check method) is lower than 0.5%, preferably, lower than 0.1%, most preferably, the weight percentage of inorganic salts is 0%.

In a preferred example of the present invention, the compound of formula 1 or salts thereof is crystalline.

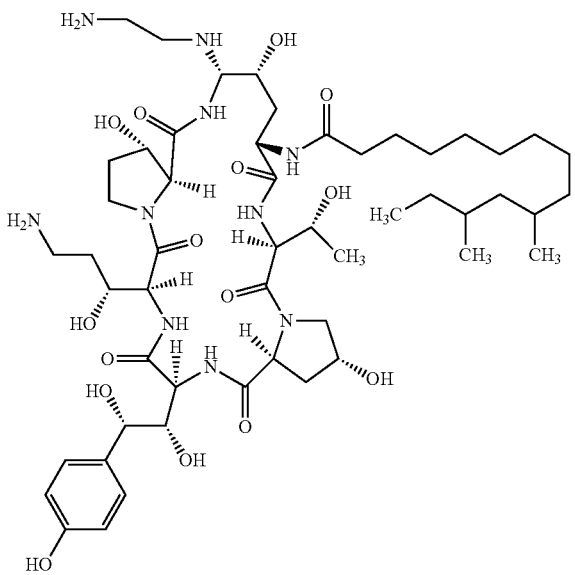

In an example of the present invention, the method for obtaining caspofungin or salts thereof with low solvent residue and hyposaline includes the following steps:
(a) vacuum-drying the raw material comprising the compound of formula 1 or salts thereof with a water system together;

(b) removing the water system, and then continually vacuum-drying the compound of formula 1 or salts thereof, thereby obtaining the compound of formula 1 or salts thereof with low solvent residue and hyposaline.

According to another preferred example, in step (a), the raw material comprising the compound of formula 1 or salts thereof is the compound of formula 1 or salts thereof in crystalline form.

According to another preferred example, in step (a), the temperature for drying ranges from 0 to 20° C.

According to another preferred example, in step (a), the water system includes tap water, pure water, ice-water mixture, trash ice, or the substance capable of releasing water vapor.

According to another preferred example, in step (a), the time for drying ranges from 1 to 48 hrs.

According to another preferred example, in step (b), the time for drying ranges from 0 to 5 hrs.

According to another preferred example, the process for preparing the compound of formula 1 or salts thereof in step (a) includes the following steps:
(a') mixing the crude preparation of the compound of formula 1 or salts thereof with acetic acid and water, thereby obtaining homogeneous solution 1;
(b') mixing homogeneous solution 1 with ethanol, thereby obtaining homogeneous solution 2; and
(c') mixing homogeneous solution 2 with ethyl acetate, thereby obtaining the raw material comprising the compound of formula 1 or salts thereof.

According to another preferred example, in step (a'), the temperature for mixing ranges from 0 to 20° C.

According to another preferred example, in step (b'), the temperature for mixing ranges from 0 to 20° C.

According to another preferred example, in step (c'), the temperature for mixing ranges from 0 to 20° C.

According to another preferred example, in step (c'), the volume ratio for mixing solution 2 with ethyl acetate is 1:1-3.

In another example of the present invention, the method for obtaining caspofungin or salts thereof with low solvent residue and hyposaline includes the following steps:
(a') mixing the compound of formula 1 or salts thereof in amorphous form with acetic acid and water, thereby obtaining homogeneous solution 1;
(b') mixing homogeneous solution 1 with the first organic solvent-ethanol, thereby obtaining homogeneous solution 2;
(c') mixing homogeneous solution 2 with the second organic solvent-ethyl acetate, thereby obtaining the crystal of compound of formula 1 or salts thereof;
(d') vacuum-drying the crystal of compound of formula 1 or salts thereof with a water system; and
(e') removing the water system, and then continually vacuum-drying the compound of formula 1 or salts thereof, thereby obtaining the compound of formula 1 or salts thereof with low solvent residue and hyposaline.

In the second aspect of the present invention, the use of caspofungin or salts thereof with low solvent residue and hyposaline provided by the present invention for preparing medicaments for the prevention or treatment of diseases caused by fungal infection is provided.

In another preferred example, a pharmaceutical composition is obtained by mixing caspofungin or salts thereof with low solvent residue and hyposaline with pharmaceutically acceptable carriers.

| Retention Time | Peak Area | Solvent |
| --- | --- | --- |
| 2.344 | 49.8 | Methanol |
| 3.097 | 152.0 | Ethanol |
| 4.069 | 20.3 | acetonitrile |
| 6.962 | 1015.7 | Ethyl acetate |
| 7.370 | 158.6 | tetrahydrofuran |

Figure 2:
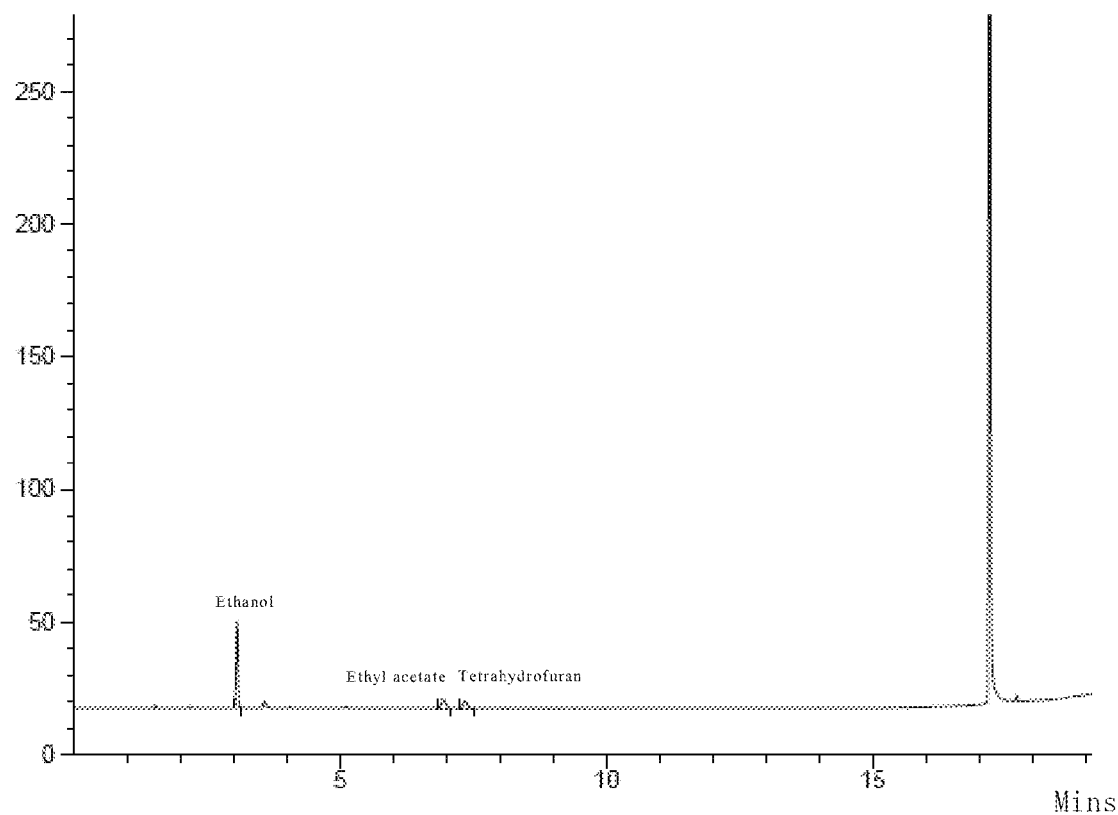

FIG. 2 indicates the GC pattern of caspofungin or salts thereof with low solvent residue and hyposaline prepared in the Examples of the present invention; wherein the retention time, peak area and weight percentage for each solvent are shown in the following table:

| Retention Time | Peak Area | Weight percentage (%) | Solvent |
| --- | --- | --- | --- |
| 2.344 | 0 | 0 | Methanol |
| 3.097 | 84.5 | 0.26 | Ethanol |
| 4.069 | 0 | 0 | acetonitrile |
| 6.962 | 19.1 | 0.01 | Ethyl acetate |
| 7.370 | 13.9 | 0.01 | tetrahydrofuran |

Figure 3:
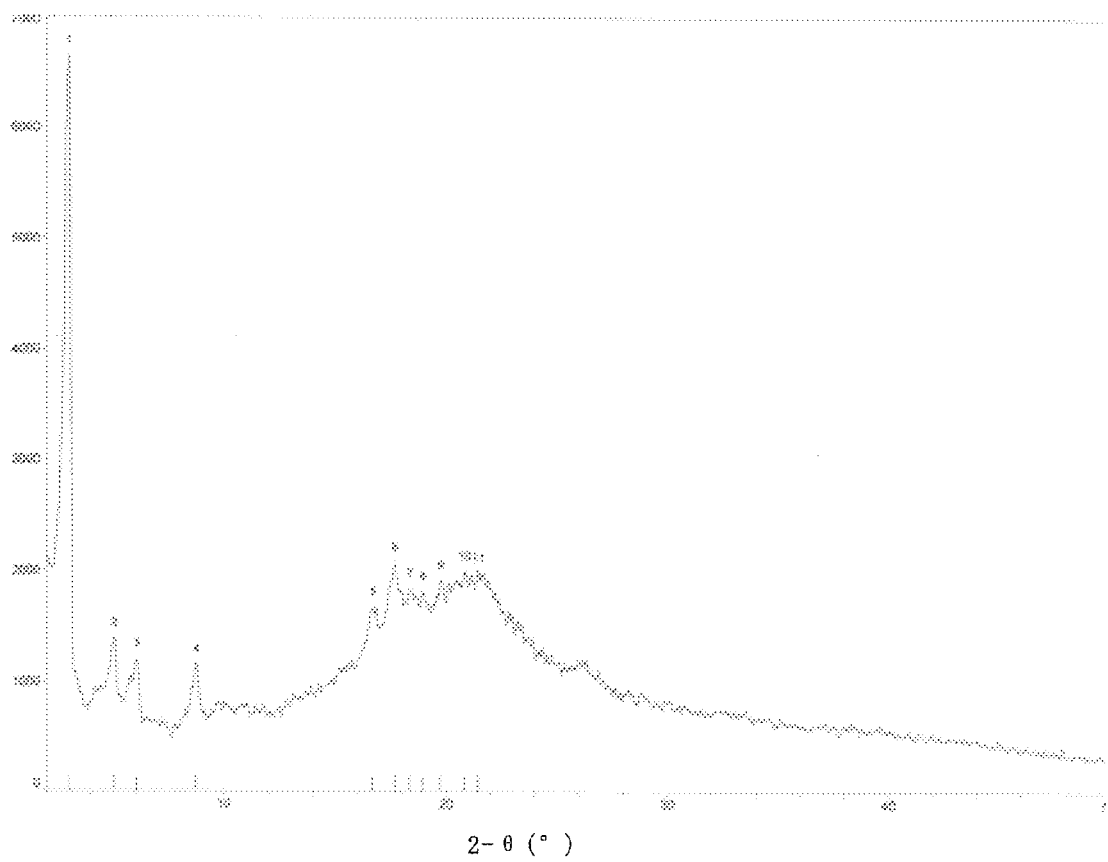

FIG. 3 indicates the XRPD pattern of caspofungin or salts thereof with low solvent residue and hyposaline prepared in the Examples of the present invention; wherein the data of each peak are shown in the following table:

| Peak No. | 2-θ (°) | d (A) | I % (Relative Intensity) |
| --- | --- | --- | --- |
| 1 | 2.980 | 29.6249 | 100 |
| 2 | 5.040 | 17.5190 | 20.8 |
| 3 | 6.040 | 14.6200 | 18.1 |
| 4 | 8.740 | 10.1093 | 17.3 |
| 5 | 16.679 | 5.3110 | 25.1 |
| 6 | 17.680 | 5.0125 | 31.0 |
| 7 | 18.360 | 4.8281 | 27.5 |
| 8 | 18.940 | 4.6817 | 27.1 |
| 9 | 19.741 | 4.4935 | 28.6 |
| 10 | 20.821 | 4.2628 | 29.8 |
| 11 | 21.439 | 4.1413 | 29.6 |

DETAILED DESCRIPTION OF THE INVENTION

The inventors have discovered a simple method for preparing caspofungin or salts thereof with low solvent residue and hyposaline. Through intensive research, the inventors have discovered that a stable caspofungin or salts thereof with low solvent residue and hyposaline can be obtained by dissolving the compound of formula 1 or salts thereof in amorphous form in aqueous acetic acid, crystallizing the compound by adding ethanol and ethyl acetate for obtaining the raw material comprising the compound of formula 1 or salts thereof, and then vacuum-drying the raw material and a water system together.

As used herein, chemical formulae or chemical names should include all of optical isomer and stereo isomer, as well as the racemic mixture comprising these isomers.

The Principle for Drying Caspofungin or Salts Thereof with Low Solvent Residue and Hyposaline The inventors have studied nitrogen-drying method, freeze-drying method, spray-drying method and vacuum-drying method (drying without water system) reported in the literatures, such as WO94/21677, WO97/47645, WO2010008493A2, WO2009151341A1, WO2010108637A1, and found that through nitrogen-drying method, freeze-drying method, spray-drying method, it is difficult to remove organic solvent, thus resulting in the excess of solvent residue, while through vacuum-drying method (drying without adding water), organic solvent can not be removed, and the product will degrade significantly. The inventors analyzed the reason for the excess of solvent residue in the product dried by using above methods and found that by using nitrogen-drying method, freeze-drying method and vacuum-drying method (drying without water system), during the early stage of drying product, organic solvent will be readily removed under the conditions of vacuum-drying or nitrogen flow. However, the crystal lattice of the sample will gradually close with the reduction of residual solvent, resulting in the retention of solvent in the crystal lattice. During the late stage of drying, the solvent will be permanently enwrapped in the crystal lattice; therefore, the solvent can not be removed under the conditions of vacuum-drying or nitrogen flow.

The inventors have surprisingly discovered that caspofungin or salts thereof with low solvent residue (even with no solvent residue) can be obtained by placing the substance capable of releasing water vapor in a vacuum dryer, and the purity of caspofungin or salts thereof won't be affected.

After obtaining caspofungin or salts thereof with low solvent residue and hyposaline, the inventors further investigated the principle of drying method according to the invention. The substance capable of releasing water vapor is placed in a vacuum dryer for controlling the water content of the sample. During the early stage of drying, great amount of organic solvent is removed. During the middle stage of drying, the water vapor is continuously formed from the water in sample, and the water vapor forms hydrogen bond with the residual solvent in sample, thereby removing the organic solvent through vacuum-drying. However, the water content in sample is limited, for maintaining the balance and preventing the crystal lattice from totally closing, the substance capable of releasing water vapor is placed in the drying system. Under vacuum condition, the substance will continuously produce water vapor, and the compound itself contains great amount of nitrogen, oxygen atoms for forming hydrogen bond with the water vapor to bind the water, thereby preventing the crystal lattice of the compound from closing and maintaining the exchange balance. Through wet nitrogen drying, another drying method in the prior art, the water content of sample can be controlled, however, the water in the sample can not produce water vapor under positive pressure, therefore, the organic solvent can not be removed together with the water through vacuum-drying, and such method has some shortcomings, such as great demand for nitrogen and high cost for the equipment.

After obtaining caspofungin or salts thereof with low solvent residue and hyposaline, the inventors further investigated the procedure of drying the compound, and surprisingly discovered that the water content of sample can be reduced to a qualified range and the sample at such range of water content has good stability, if the sample is dried for another period of time under vacuum after the amount of organic solvent is qualified through drying and the substance capable of releasing water vapor is removed. Therefore, the drying process according to the present invention can be divided into two phase: in the first phase, vacuum-drying the sample with the water system for removing organic solvent; and in the second phase, the water system is removed, and then the sample is continually vacuum-dried until the water content of the sample is eligible.

Determination of the Purity and Solvent Residue of Caspofungin or Salts Thereof with Low Solvent Residue and Hyposaline After obtaining caspofungin or salts thereof with low solvent residue and hyposaline, the inventors further investigated the purity and solvent residue thereof through HPLC and GC.

In the present invention, HPLC is used to determine the purity of caspofungin or salts thereof (the compound of formula 1 or salts thereof), and to investigate the stability of sample. Said HPLC is described as follows:

Chromatographic column: 4.6×250 mm, 5 μm C18 column;

Mobile phase: A: 0.1% aqueous perchloric acid and 0.075% aqueous sodium chloride; B: acetonitrile;

Gradient elution conditions: A:B=65.5:34.5, 14.5 mins; A:B=65.5:34.5 to 50:50, 21.5 mins; A:B=50:50 to 35:65, 10 mins; A:B=35:65 to 20:80, 5 mins; A:B=20:80, 2 mins; A:B=20:80 to 65.5:34.5, 1 mins; A:B=65.5:34.5, 13 mins;

Flow rate: 1.0 ml/min; Injection volume: 10 μL;

Column temperature: 35° C.±5° C.; Detection wavelength: 220 nm; Running time: 60 mins;

Retention time of major peak: about 27 min;

In the present invention, GC is used to determine the solvent residue of the sample prepared by the method according to the invention. Said GC is described as follows:

Chromatographic column: Varian CP-Select 624 (94% cyanopropylphenyl-6% dimethylpolysiloxane);

Specification of the column: 30 m×0.32 mm×1.8 μm;

Inlet temperature: 200° C.

Detector temperature: 260° C.

Flow rate: 2.5 ml/min, Constant flow;

Furnace temperature:

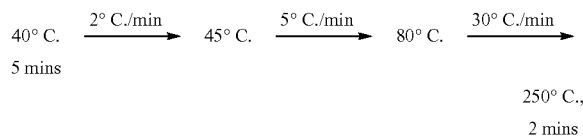

250° C., 2 mins

Carrier gas: nitrogen;

Split ratio: 1:1 (workstation), actual split ratio: 17:1 (measurement from soap film flowmeter)

Gas in the detector: Air flow: 400 ml/min

Hydrogen flow: 40 ml/min

End purge gas flow: 25 ml/min (nitrogen)

Conditions for headspace injector:

Heating equilibrium temperature: 80° C.; Sample loop temperature: 85° C.;

Transmission line temperature: 90° C.;

Balance time: 20 mins; pressure time: 0.5 min; charging time: 0.2 min;

Balance time for sample loop: 0.10 min; injecting time: 1 min; running time: 30 mins;

Injection volume: 1 ml.

In the present invention, residue on ignition check method is used to determine the salt residue in the sample prepared by the method of the present invention. The method is described as follows:

The sample is mixed with sulfuric acid, the resulting mixture is heated in an electric furnace to 600-700° C. and then cooled in a vacuum-dryer to room temperature, the weight of residue is weighed, and the amount of organic salts is calculated.

Preparation Method

Through intensive research, the inventors have discovered that a stable caspofungin or salts thereof with low solvent residue and hyposaline can be obtained by dissolving the amorphous caspofungin in acetic acid and water for forming a homogeneous solution, adding ethanol for diluting the solution, using ethyl acetate for further diluting the resulting solution, obtaining the raw material comprising the compound of formula 1 or salts thereof by altering the factors, such as the temperature for crystallization, molar concentration, cooling rate or stirring conditions, or the time for crystallization, and then vacuum-drying the raw material with a water system together.

As used herein, "the crude preparation of the compound of formula 1 or salts thereof" or "the crude preparation of caspofungin or salts thereof" can be used interchangeably, and both refer to the compound of formula 1 or salts thereof in amorphous form, which can be obtained by well-known methods in the art, for example (but not limited to), the methods reported in the literatures, such as J. Org. Chem., 2007, 72, 2335-2343, WO2009158034 A1.

As used herein, "the raw material comprising the compound of formula 1 or salts thereof" refers to the compound of formula 1 or salts thereof in crystalline form, which can be obtained by the following steps:

a'. mixing the crude preparation of the compound of formula 1 or salts thereof with acetic acid and water, thereby obtaining homogeneous solution 1;

b'. mixing homogeneous solution 1 with ethanol, thereby obtaining homogeneous solution 2; and c'. mixing homogeneous solution 2 with ethyl acetate, thereby obtaining the raw material comprising the compound of formula 1 or salts thereof The above steps a'-b'-c' can be repeated for 1, 2 or 3 times for obtaining the re-crystallized compound of formula 1 or salts thereof. The weight percentage of organic solvent in the compound of formula 1 or salts thereof in crystalline form is ≥1.5%. Said organic solvent is tetrahydrofuran, acetonitrile, methanol, ethyl acetate or ethanol.

In the method for obtaining the raw material comprising the compound of formula 1 or salts thereof, once the crystallization of step (c') is completed, the crystals can be separated by filtration, decantation of solvent or other methods, with filtration being preferred.

The method for preparing caspofungin or salts thereof with low solvent residue and hyposaline includes the following steps:

(a) vacuum-drying the raw material comprising the compound of formula 1 or salts thereof with a water system together;

(b) removing the water system, and then continually vacuum-drying the raw material comprising the compound of formula 1 or salts thereof, thereby obtaining the compound of formula 1 or salts thereof with low solvent residue and hyposaline.

According to another preferred example, in step (a), the temperature for drying ranges from 0 to 20° C.

According to another preferred example, in step (a), the water system includes tap water, pure water, ice-water mixture, or the substance capable of releasing water vapor.

According to another preferred example, in step (a), the time for drying ranges from 1 to 48 hrs.

According to another preferred example, in step (b), the time for drying ranges from 0 to 5 hrs.

According to another preferred example, the process for preparing the raw material comprising the compound of formula 1 or salts thereof in step (a) can include the following steps:
- (a') mixing the crude preparation of the compound of formula 1 or salts thereof with acetic acid and water, thereby obtaining homogeneous solution 1;
- (b') mixing homogeneous solution 1 with ethanol, thereby obtaining homogeneous solution 2; and
- (c') mixing homogeneous solution 2 with ethyl acetate, thereby obtaining the raw material comprising the compound of formula 1 or salts thereof.

According to another preferred example, in step (a'), the temperature for mixing ranges from 0 to 20° C.

According to another preferred example, in step (b'), the temperature for mixing ranges from 0 to 20° C.

According to another preferred example, in step (c'), the temperature for mixing ranges from 0 to 20° C.

According to another preferred example, in step (c'), the volume ratio for mixing solution 2 with ethyl acetate is 1:1-3.

In another preferred example of the present invention, the method includes:
- (a') mixing the crude preparation of the compound of formula 1 or salts thereof with acetic acid and water, thereby obtaining homogeneous solution 1;
- (b') mixing homogeneous solution 1 with the first organic solvent-ethanol, thereby obtaining homogeneous solution 2;
- (c') mixing homogeneous solution 2 with the second organic solvent-ethyl acetate, thereby obtaining the raw material comprising the compound of formula 1 or salts thereof;
- (d') vacuum-drying the raw material comprising the compound of formula 1 or salts thereof obtained in step c' with a water system; and
- (e') removing the water system, and then continually vacuum-drying the raw material comprising the compound of formula 1 or salts thereof, thereby obtaining the compound of formula 1 or salts thereof with low solvent residue and hyposaline.

Once the crystallization of step (c') is completed, the crystals can be separated by filtration, decantation of solvent or other methods, with filtration being preferred. Then, the crystal can be optionally washed, and finally, the crystal and a water system are dried under vacuum for obtaining caspofungin or salts thereof with low solvent residue and hyposaline.

In the method provided by the present invention for obtaining the compound of formula 1 or salts thereof with low solvent residue and hyposaline, "vacuum-drying the raw material comprising the compound of formula 1 or salts thereof with a water system together" means that the raw material comprising the compound of formula 1 or salts thereof will be placed in the position where a sample is generally put in a vacuum-dryer, and an open container comprising the substance capable of releasing water vapor is placed in the environment of the vacuum-dryer, (for example, at the bottom of the vacumm-dryer). Said substance capable of releasing water vapor is selected from tap water, pure water, trash ice, or ice-water mixture.

In the method provided by the present invention for obtaining the compound of formula 1 or salts thereof with low solvent residue and hyposaline, "removing the water system" means that the open container comprising the substance capable of releasing water vapor is removed out of the vacuum-dryer.

Use

In the second aspect of the present invention, the use of caspofungin or salts thereof with low solvent residue and hyposaline provided by the present invention for preparing medicaments for the prevention or treatment of diseases caused by fungal infection is provided.

Therefore, a pharmaceutical composition is further provided by the present invention, comprising caspofungin or salts thereof with low solvent residue and hyposaline and pharmaceutically acceptable carriers.

As used herein, the term "efficient amount" means the carriers for administering the therapeutic agents, including various of excipients and diluents. The term means such drug carriers that they, per se, are not necessary active ingredients, and do not have undue toxicity. Suitable carriers are well-known to a person skilled in the art. Detailed discussion on the pharmaceutically acceptable excipients can be found in *Remington's Pharmaceutical Sciences* (Mack Pub. Co., N.J., 1991). As to caspofungin or salts thereof, the pharmaceutically acceptable carriers include liquid, such as water, saline, glycerol, or ethanol. Moreover, these carriers can be used with auxiliary agents, such as disintegrant, wetting agent, emulsifying agent, pH buffer, and the like.

The medicament-caspofungin can be prepared into various of dosage forms according to different administration routes. These dosage forms can be administered through the following modes: oral administration, spray inhalation, rectal administration, nasal delivery, buccal administration, local administration, parenteral administration, such as subcutaneous, intravenous, intramuscular, intraperitoneal, intrathecal, intraventricular, intrasternal, or intracranial injection or infusion, or by means of explant reservoir.

All the features mentioned above or in the examples below of the invention can be optionally combined. All of the features disclosed in this specification can be used in combination with any form of caspofungin. Any alternative feature serving the same, equivalent, or similar purpose may replace each feature disclosed in this specification. Therefore, unless otherwise specified, the features as disclosed are only general examples of equivalent or similar features.

The main advantages of the invention include:

1. A novel caspofungin or pharmaceutically acceptable salts thereof with low solvent residue and hyposaline is provided by the present invention.

2. A method for preparing caspofungin or salts thereof with low solvent residue and hyposaline is provided by the present invention.

3. The present invention has advantages, such as mild conditions, simple operation, high yield, stable product, convenience of transportation, thereby greatly reducing the difficulties in technical operation and the production cost.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution. Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

Example 1

Preparation of the Raw Material Comprising the Compound of Formula 1 in Crystalline Form According to the methods reported in the literatures, such as WO97/47645, U.S. Pat. No. 5,936,062, J. Org. Chem., 2007, 72, 2335-2343, the raw material comprising the compound of formula 1 was prepared by using Pneumocandin $B_0$ as starting material.

Example 2

Preparation of the Compound of Formula 1 in Amorphous Form

The compound of formula 1 in amorphous form was prepared according to the lyophilization methods reported in the literatures, such as J. Org. Chem., 2007, 72, 2335-2343, WO2009158034 A1. Alternatively, the compound of formula 1 in amorphous form was obtained by directly concentrating eluate from column chromatography under reduced pressure to almost dry.

Example 3

Figure 1:
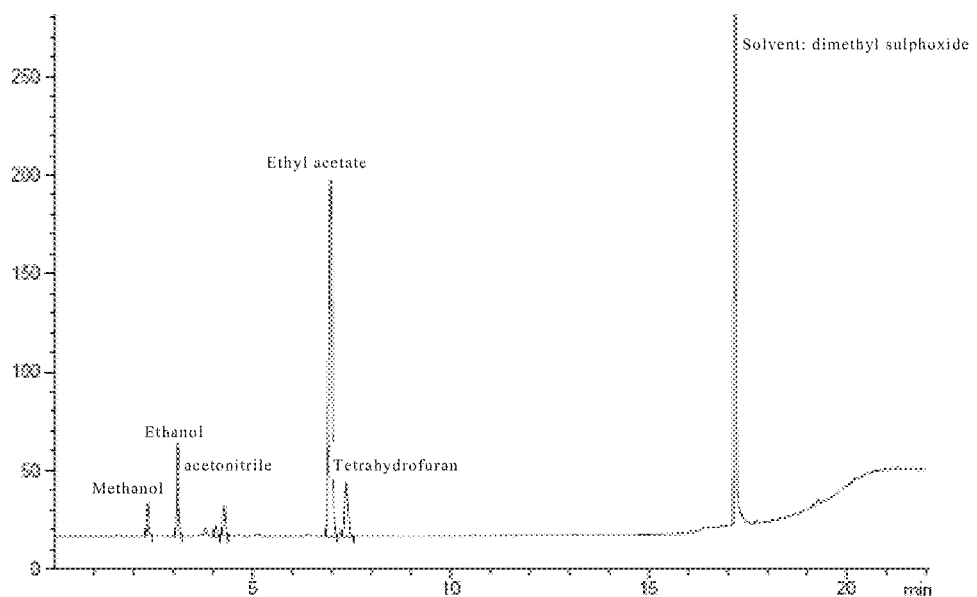
FIG. 1 indicates the GC pattern of solvents in the present invention; wherein the retention time and neak area for each solvent are shown in the following table.

Preparation of Caspofungin or Salts thereof with Low Solvent Residue and Hyposaline At 12° C., the compound of formula 1 (2.0 g) obtained in example 2 was dissolved into a system comprising acetic acid (0.13 ml) and water (2.2 ml). Upon dissolution, ethanol (25 ml) was added, and the resulting mixture was stirred to homogeneous. Ethyl acetate (27.4 ml) was slowly added dropwise. Upon addition, the resulting mixture was stirred at 12° C. for 12 h. Caspofungin was filtered out and washed with the mixture of ethanol and ethyl acetate (1.7:1) for several times. Then, the sample was placed into a vacuum-dryer, and put a plate of tap water on the bottom of the vacuum-dryer. The whole system was dried at 12° C. and under vacuum for 2 h. The plate of tap water was removed, and the sample was dried at 12° C. and under vacuum for another 2 h, thereby obtaining caspofungin diacetate (1.50 g, yield 75%). The purity of the obtained caspofungin was determined as 99.90% by HPLC; the content of single impurity was lower than 0.1%; the weight percentage of tetrahydrofuran, acetonitrile, methanol, ethyl acetate and ethanol was 0.01%, 0.0%, 0.0%, 0.01% and 0.26%, respectively (see FIGS. 1 and 2); the weight percentage of inorganic salts was 0.0%; and, the water content was 7.5%. XRPD pattern of the sample was shown in FIG. 3.

MS (ESI): 1093.6 [M+H]$^+$;

$^1$H-NMR (500.13 MHz, CD$_3$OD) δ 7.12 (m, 2H), 6.75 (m, 2H), 4.97 (d, 1H), 4.91 (d, 1H), 4.66 (d, 1H), 4.60 (dd, 3.2, 1H), 4.56-4.51 (om, 2H), 4.48 (dd, 1H), 4.32-4.28 (om, 3H) 4.22 (dd, 1H), 4.18 (d, 1H), 4.08-3.96 (om, 3H), 3.83 (m, 1H), 3.76 (d, 1H), 3.05 (t, 2H), 3.02-2.76 (om, 4H), 2.41 (dd, 1H), 2.29-2.17 (om, 3H) 2.11-1.78 (om, 5H), 1.90 (s, 6H), 1.58 (m, 2H), 1.53-1.19 (om, 15H), 1.16 (d, 3H), 1.13-1.00 (om, 2H), 0.91 (m, 1H), 0.87 (t, 3H), 0.85 (degenerate d, 6H);

$^{13}$C-NMR (125 MHz, CD$_3$OD) 179.3, 175.5, 173.4, 172.8, 172.6, 171.95, 171.93, 168.1, 157.7, 132.1, 128.8, 115.4, 76.5, 74.8, 74.2, 71.2, 70.5, 69.3, 68.5, 67.4, 63.5, 61.9, 57.6, 56.3, 55.4, 55.2, 50.4, 46.2, 45.1, 43.1, 39.6, 38.1, 37.6, 37.2, 36.1, 34.9, 33.8, 32.1, 30.4, 30.3, 30.0, 29.9, 29.8, 29.53, 29.50, 27.2, 26.3, 23.3, 19.9, 19.4, 19.1.

Example 4

Preparation of Caspofungin with Low Solvent Residue and Hyposaline

At 10° C., the compound of formula 1 (2.0 g) obtained in example 2 was dissolved into a system comprising acetic acid (0.13 ml) and water (2.2 ml). Upon dissolution, ethanol (25 ml) was added, and the resulting mixture was stirred to homogeneous. Ethyl acetate (27.4 ml) was slowly added dropwise. Upon addition, the resulting mixture was stirred at 10° C. for 2 h. Caspofungin was filtered out, and washed with the mixture of ethanol and ethyl acetate (1.7:1) for several times. Then, the sample was placed into a vacuum-dryer, and a plate of tap water was put on the bottom of the vacuum-dryer. The whole system was dried at 10° C. and under vacuum for 4 h, thereby obtaining caspofungin diacetate (1.50 g, yield 75%). The purity of the obtained caspofungin was determined as 99.90% by HPLC; the content of single impurity was lower than 0.1%; the weight percentage of tetrahydrofuran, acetonitrile, methanol, ethyl acetate and ethanol was 0.07%, 0.04%, 0.15%, 0.47% and 0.49%, respectively; the weight percentage of inorganic salts was 0.095%; and, the water content was 9.5%.

Example 5

Preparation of Caspofungin with Low Solvent Residue and Hyposaline

At 15° C., the raw material comprising the compound of formula 1 obtained in example 1 (2.0 g) was dissolved into a system comprising acetic acid (0.25 ml) and water (2.2 ml). Upon dissolution, ethanol (25 ml) was added, and the resulting mixture was stirred to homogeneous. Ethyl acetate (30 ml) was slowly added dropwise. Upon addition, the resulting mixture was stirred at 15° C. for 2 h. Caspofungin was filtered out, and washed with the mixture of ethanol and ethyl acetate (1.7:1) for several times. Then, the sample was placed into a vacuum-dryer, and a plate of pure water was put on the bottom of the vacuum-dryer. The whole system was dried at 15° C. and under vacuum for 6 h. The plate of pure water was then removed, and the sample was dried at 15° C. and under vacuum for another 2 h, thereby obtaining caspofungin diacetate (1.70 g, yield 85%). The purity of the obtained caspofungin was determined as 99.91% by HPLC; the weight percentage of tetrahydrofuran, acetonitrile, methanol, ethyl acetate and ethanol was 0.05%, 0.02%, 0.29%, 0.48% and 0.50%, respectively; the weight percentage of inorganic salts was 0.495%; and, the water content was 8.5%.

Example 6

Preparation of Caspofungin with Low Solvent Residue and Hyposaline

At 20° C., the raw material comprising the compound of formula 1 obtained in example 1 (2.0 g) was dissolved into a system comprising acetic acid (0.13 ml) and water (4.2 ml). Upon dissolution, ethanol (25 ml) was added, and the resulting mixture was stirred to homogeneous. Ethyl acetate (88.2 ml) was slowly added dropwise. Upon addition, the resulting mixture was stirred at 20° C. for 1 h. Caspofungin was filtered out, and washed with the mixture of ethanol and ethyl acetate (1.7:1) for several times. Then, the sample was placed into a vacuum-dryer, and a plate of ice-water mixture was put on the bottom of the vacuum-dryer. The whole system was dried at 20° C. and under vacuum for 10 h. The plate of ice-water mixture was then removed, and the sample was dried at 20° C. and under vacuum for another 1 h, thereby obtaining caspofungin diacetate (1.95 g, yield 97.5%). The purity of the obtained caspofungin was determined as 99.92% by HPLC; the weight percentage of tetrahydrofuran, acetonitrile, methanol, ethyl acetate and ethanol was 0.02%, 0.01%, 0.15%, 0.26% and 0.25%, respectively; the weight percentage of inorganic salts was 0%; and, the water content was 8.9%.

Example 7

Preparation of Caspofungin with Low Solvent Residue and Hyposaline

At 10° C., the compound of formula 1 obtained in example 2 (2.0 g) was dissolved into a system comprising acetic acid (0.5 ml) and water (2.2 ml). Upon dissolution, ethanol (25 ml) was added, and the resulting mixture was stirred to homogeneous. Ethyl acetate (30 ml) was slowly added dropwise. Upon addition, the resulting mixture was stirred at 10° C. for 2 h. Caspofungin was filtered out, and washed with the mixture of ethanol and ethyl acetate (1.7:1) for several times. Then, the sample was placed into a vacuum-dryer, and a plate of ice-water mixture was put on the bottom of the vacuum-dryer. The whole system was dried at 10° C. and under vacuum for 24 h. The plate of ice-water mixture was removed, and the sample was dried at 10° C. and under vacuum for another 2.5 h, thereby obtaining caspofungin diacetate (1.55 g, yield 77.5%). The purity of the obtained caspofungin was determined as 99.90% by HPLC; the weight percentage of tetrahydrofuran, acetonitrile, methanol, ethyl acetate and ethanol was 0%, 0%, 0.05%, 0.09% and 0.10%, respectively; the weight percentage of inorganic salts was 0%; and, the water content was 9.0%.

Example 8

Preparation of Caspofungin with Low Solvent Residue and Hyposaline

At 0° C., the compound of formula 1 obtained in example 2 (2.0 g) was dissolved into a system comprising acetic acid (0.13 ml) and water (2.3 ml). Upon dissolution, ethanol (36 ml) was added, and the resulting mixture was stirred to homogeneous. Ethyl acetate (38.4 ml) was slowly added dropwise. Upon addition, the resulting mixture was stirred at 0° C. for 1 h. Caspofungin was filtered out, and washed with the mixture of ethanol and ethyl acetate (1.7:1) for several times. Then, the sample was placed into a vacuum-dryer, and a plate of ice-water mixture was put on the bottom of the vacuum-dryer. The whole system was dried at 0° C. and under vacuum for 48 h. The plate of ice-water mixture was removed, and the sample was dried at 0° C. and under vacuum for another 5 h, thereby obtaining caspofungin diacetate (1.80 g, yield 90%). The purity of the obtained caspofungin was determined as 99.88% by HPLC; each weight percentage of tetrahydrofuran, acetonitrile, methanol, ethyl acetate and ethanol was 0%; the weight percentage of inorganic salts was 0%; and, the water content was 12.0%.

Example 9

Preparation of Caspofungin with Low Solvent Residue and Hyposaline

At 5° C., the raw material comprising the compound of formula 1 obtained in example 1 (2.0 g) was dissolved into a system comprising acetic acid (0.50 ml) and water (3.3 ml). Upon dissolution, ethanol (36 ml) was added, and the resulting mixture was stirred to homogeneous. Ethyl acetate (60 ml) was slowly added dropwise. Upon addition, the resulting mixture was stirred at 5° C. for 1 h. Caspofungin was filtered out, and washed with the mixture of ethanol and ethyl acetate (1.7:1) for several times. Then, the sample was placed into a vacuum-dryer, and a plate of trash ice was put on the bottom of the vacuum-dryer. The whole system was dried at 5° C. and under vacuum for 48 h. The plate of trash ice was removed, and the sample was dried at 5° C. and under vacuum for another 0.5 h, thereby obtaining caspofungin diacetate (1.88 g, yield 94.0%). The purity of the obtained caspofungin was determined as 99.86% by HPLC; each weight percentage of tetrahydrofuran, acetonitrile, methanol, ethyl acetate and ethanol was 0%; the weight percentage of inorganic salts was 0%; and, the water content was 15.0%.

Example 10

Preparation of Caspofungin with Low Solvent Residue and Hyposaline

The raw material comprising the compound of formula 1 obtained in example 1 was placed into a vacuum-dryer, and a plate of trash ice was put on the bottom of the vacuum-dryer. The whole system was dried at 0° C. and under vacuum for 24 h. The plate of trash ice was removed, and the sample was dried at 0° C. and under vacuum for another 1 h. The purity of the obtained caspofungin was determined as 99.50% by HPLC; the weight percentage of tetrahydrofuran, acetonitrile, methanol, ethyl acetate and ethanol was 0.01%, 0.03%, 0.10%, 0.19% and 0.20%, respectively; the weight percentage of inorganic salts was 0.05%; and, the water content was 9.5%.

Example 11

Preparation of Caspofungin with Low Solvent Residue and Hyposaline

The raw material comprising the compound of formula 1 obtained in example 1 was placed into a vacuum-dryer, and a plate of trash ice was put on the bottom of the vacuum-dryer. The whole system was dried at 10° C. and under vacuum for 12 h. The plate of trash ice was removed, and the sample was dried at 10° C. and under vacuum for another 0.5 h. The purity of the obtained caspofungin was determined as 99.50% by HPLC; the weight percentage of tetrahydrofuran, acetonitrile, methanol, ethyl acetate and ethanol was 0.01%, 0.02%, 0.10%, 0.15% and 0.15%, respectively; the weight percentage of inorganic salts was 0.05%; and, the water content was 10.2%.

Comparative Example 12

Study on the Stability of Caspofungin with Low Solvent Residue and Hyposaline The samples prepared in the above example 3, example 4, example 5, example 6, example 7, example 8 and example 9 were stored at −25-20° C. for 30 days. And then HPLC analysis was applied on these samples. The HPLC results are shown in the following table 1. According to the HPLC analysis, the stability of the samples was good, and no degradation occured.

| Sample | Initial purity | Storing condition | Storing time (days) | Purity |
|---|---|---|---|---|
| Example 3 | 99.90% | −25~−20° C. | 30 | 99.90% |
| Example 4 | 99.90% | −25~−20° C. | 30 | 99.90% |
| Example 5 | 99.91% | −25~−20° C. | 30 | 99.91% |
| Example 6 | 99.92% | −25~−20° C. | 30 | 99.92% |
| Example 7 | 99.90% | −25~−20° C. | 30 | 99.90% |
| Example 8 | 99.88% | −25~−20° C. | 30 | 99.88% |
| Example 9 | 99.86% | −25~−20° C. | 30 | 99.86% |

Comparative Example 13

Preparation of Caspofungin According to the Methods in the Literatures

According to the methods reported in the literatures, such as WO97/47645, U.S. Pat. No. 5,936,062, J. Org. Chem., 2007, 72, 2335-2343, the crude preparation of caspofungin was prepared by using Pneumocandin $B_0$ as starting material. Then, the caspofungin sample with purity of 99.9% was obtained by crystallization and separation using preparative column. The sample was dried or crystallized according to the methods reported in the literatures, such as WO94/21677, WO97/47645, WO2010008493 A2, WO2009151341 A1, WO2010108637 A1, respectively (data shown in the following table). According to the data, organic solvent can not be removed through wet nitrogen-drying method, freeze-drying method and spray-drying method, thus resulting in the excess of solvent residue; through vacuum-drying method (drying without adding water system), organic solvent can not be removed, and the product will degrade significantly; and through salting-out crystallization, there is no organic solvent in the product, however, the content of sodium chloride is significantly beyond the criterion, and upon crystallization, the purity of the product is reduced.

Example 14

Preparation of the Pharmaceutical Composition Comprising Caspofungin with Low Solvent Residue and Hyposaline

| ingredients | Amount |
|---|---|
| Caspofungin with low solvent residue and hyposaline obtained in example 7 (the weight percentage of tetrahydrofuran, acetonitrile, methanol, ethyl acetate and ethanol was 0%, 0%, 0.05%, 0.09% and 0.10%, respectively; the weight percentage of inorganic salts was 0%; and, the water content was 9.0%) | 46.6 mg/ml (concentration of caspofungin acetate) |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.375 g of sucrose, 0.25 g of mannitol, 8.75 ml of water, 0.25 ml of aqueous acetic acid (75 mg/ml) were added. Then, caspofungin with low solvent residue and hyposaline obtained in example 7 (0.6415 g) was added. The resulting mixture solution was stirred to homogeneous, pH value of the solution was adjusted to 6 by using 1 N aqueous sodium hydroxide, and the volume of the mixture solution was adjusted to 12.5 ml. The solution was filtered by using an aseptic filter, and the filtrate was transferred into 10 ml glass tubes, with each tube containing 1.75 ml. The tubes were transferred into a freeze dryer, thereby lyophilizing the filtrate into white powder.

Example 15

Preparation of the Pharmaceutical Composition Comprising Caspofungin with Low Solvent Residue and Hyposaline

| ingredients | Amount |
|---|---|
| Caspofungin with low solvent residue and hyposaline obtained in example 9 (each weight percentage of tetrahydrofuran, acetonitrile, methanol, ethyl acetate and ethanol was 0%; the weight percentage of inorganic salts was 0% and, the water content was 15.0%) | 46.6 mg/ml (concentration of caspofungin acetate) |

| | tetrahydrofuran | acetonitrile | methanol | Ethyl acetate | ethanol | Inorganic salts | Water content | HPLC purity |
|---|---|---|---|---|---|---|---|---|
| wet nitrogen-drying method | 0.07% | 0.14% | 0.25% | 1.0% | 2.5% | 0.05% | 8.8% | 99.7% |
| freeze-drying method | 0.05% | 0.09% | 0.27% | 1.2% | 2.3% | 0% | 3.8% | 99.6% |
| spray-drying method | 0.02% | 0.14% | 0.29% | 1.5% | 2.9% | 0% | 5.8% | 99.6% |
| vacuum-drying method (drying without adding water system) | 0.01% | 0.03% | 0.04% | 0.75% | 1.24% | 0% | 2.0% | 99.1% |
| salting-out crystallization | 0% | 0% | 0% | 0% | 0% | 1.55% | 7.8% | 99.6% |

-continued

| ingredients | Amount |
| --- | --- |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.375 g of sucrose, 0.25 g of mannitol, 8.75 ml of water, 0.25 ml of aqueous acetic acid (75 mg/ml) were added. Then, caspofungin with low solvent residue and hyposaline obtained in example 9 (0.6853 g) was added. The resulting mixture solution was stirred to homogeneous, pH value of the solution was adjusted to 6 by using 1 N aqueous sodium hydroxide, and the volume of the mixture solution was adjusted to 12.5 ml. The solution was filtered by using an aseptic filter, and the filtrate was transferred into 10 ml glass tubes, with each tube containing 1.75 ml. The tubes were transferred into a freeze dryer, thereby lyophilizing the filtrate into white powder.

Example 16

Preparation of the Pharmaceutical Composition Comprising Caspofungin with Low Solvent Residue and Hyposaline

| ingredients | Amount |
| --- | --- |
| Caspofungin with low solvent residue and hyposaline obtained in example 4 (the weight percentage of tetrahydrofuran, acetonitrile, methanol, ethyl acetate and ethanol was 0.07%, 0.04%, 0.15%, 0.47% and 0.49%, respectively; the weight percentage of inorganic salts was 0.095%; and, the water content was 9.5%) | 46.6 mg/ml (concentration of caspofungin acetate) |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.375 g of sucrose, 0.25 g of mannitol, 8.75 ml of water, 0.25 ml of aqueous acetic acid (75 mg/ml) were added. Then, caspofungin with low solvent residue and hyposaline obtained in example 4 (0.6388 g) was added. The resulting mixture solution was stirred to homogeneous, pH value of the solution was adjusted to 6 by using 1 N aqueous sodium hydroxide, and the volume of the mixture solution was adjusted to 12.5 ml. The solution was filtered by using an aseptic filter, and the filtrate was transferred into 10 ml glass tubes, with each tube containing 1.75 ml. The tubes were transferred into a freeze dryer, thereby lyophilizing the filtrate into white powder.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

The invention claimed is:

1. A preparation method for a composition comprising: a compound of formula 1 or salts thereof; one or more organic solvents resulting from the preparation of the compound of formula 1 or salts thereof; and inorganic salts, wherein, in the one or more organic solvents, each organic solvent is present at a weight percentage of not more than 0.5%; the salts of the compound of formula 1 are acetate; and the inorganic salts are present at a weight percentage of not more than 0.5%, wherein the method includes the following steps:

a. vacuum-drying raw material comprising the compound of formula 1 or salts thereof with a water system together,

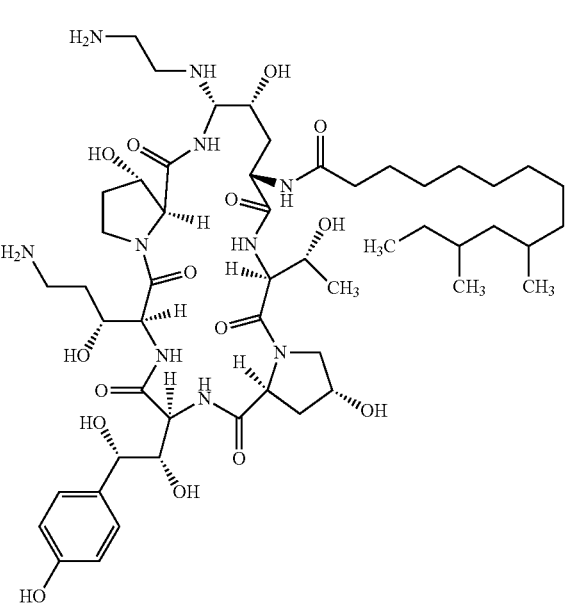

b. removing the water system, and then continuing vacuum-drying of the raw material comprising the compound of formula 1 or salts thereof, thereby obtaining the composition.

2. The preparation method according to claim 1, wherein, in step a, a temperature for drying ranges from 0 to 20° C.

3. The preparation method according to claim 1, wherein, in step a, the water system includes tap water, pure water, ice-water mixture, or a substance capable of releasing water vapor.

4. The preparation method according to claim 1, wherein, in step a, a time for drying ranges from 1 to 48 hrs.

5. The preparation method according to claim 1, wherein, in step b, a time for drying ranges from 0 to 5 hrs.

6. The preparation method according to claim 1, wherein the process for preparing a raw material comprising the compound of formula 1 or salts thereof in step a comprises:

a'. mixing a crude preparation of the compound of formula 1 or salts thereof with acetic acid and water, thereby obtaining homogeneous solution 1;

b'. mixing homogeneous solution 1 with ethanol, thereby obtaining homogeneous solution 2; and c'. mixing homogeneous solution 2 with ethyl acetate, thereby obtaining caspofungin or salts thereof in crystalline form.

7. The preparation method according to claim 6, wherein, in step a', a temperature for mixing ranges from 0 to 20° C.

8. The preparation method according to claim 6, wherein, in step b', a temperature for mixing ranges from 0 to 20° C.

9. The preparation method according to claim 6, wherein, in step c', a temperature for mixing ranges from 0 to 20° C.

10. The preparation method according to claim 6, wherein, in step c', a volume ratio for mixing homogeneous solution 2 with ethyl acetate is 1:1-3.

* * * * *